(12) United States Patent
Völkel et al.

(10) Patent No.: US 7,320,803 B2
(45) Date of Patent: Jan. 22, 2008

(54) CRYSTALLINE CHOLINE ASCORBATE

(75) Inventors: Ludwig Völkel, Limburgerhof (DE);
Alfred Oftring, Bad Dürkheim (DE);
Oliver Hasselwander, Landau (DE);
Ulrike Sindel, München (DE); Klaus Krämer, Landau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/076,514

(22) Filed: Feb. 19, 2002

(65) Prior Publication Data
US 2002/0161039 A1 Oct. 31, 2002

(30) Foreign Application Priority Data
Feb. 23, 2001 (DE) .................. 101 09 073

(51) Int. Cl.
*C07C 213/00* (2006.01)

(52) U.S. Cl. .................. 424/489; 424/442; 514/474; 564/293

(58) Field of Classification Search .................. 424/177, 424/115, 329, 283, 400, 405, 489, 442; 564/293; 514/474
See application file for complete search history.

(56) References Cited

U.S. PATENT DOCUMENTS

| 2,774,759 | A | * | 12/1956 | Blackett et al. .......... 260/251.5 |
| 2,832,166 | A | | 2/1958 | Hoffman |
| 2,870,198 | A | * | 1/1959 | Klein et al. .................. 260/501 |
| 4,394,377 | A | * | 7/1983 | Spires ........................ 424/177 |

FOREIGN PATENT DOCUMENTS

| CH | 490 322 | 5/1970 |
| EP | 812 821 | 12/1997 |

* cited by examiner

*Primary Examiner*—Michael G. Hartley
*Assistant Examiner*—Micah-Paul Young
(74) *Attorney, Agent, or Firm*—Novak Druce & Quigg, LLP

(57) ABSTRACT

Crystalline ascorbate, in particular choline ascorbate in the form of crystals free from water of crystallization, processes for its preparation, and its used are described.

3 Claims, 1 Drawing Sheet

2-Theta-Scale

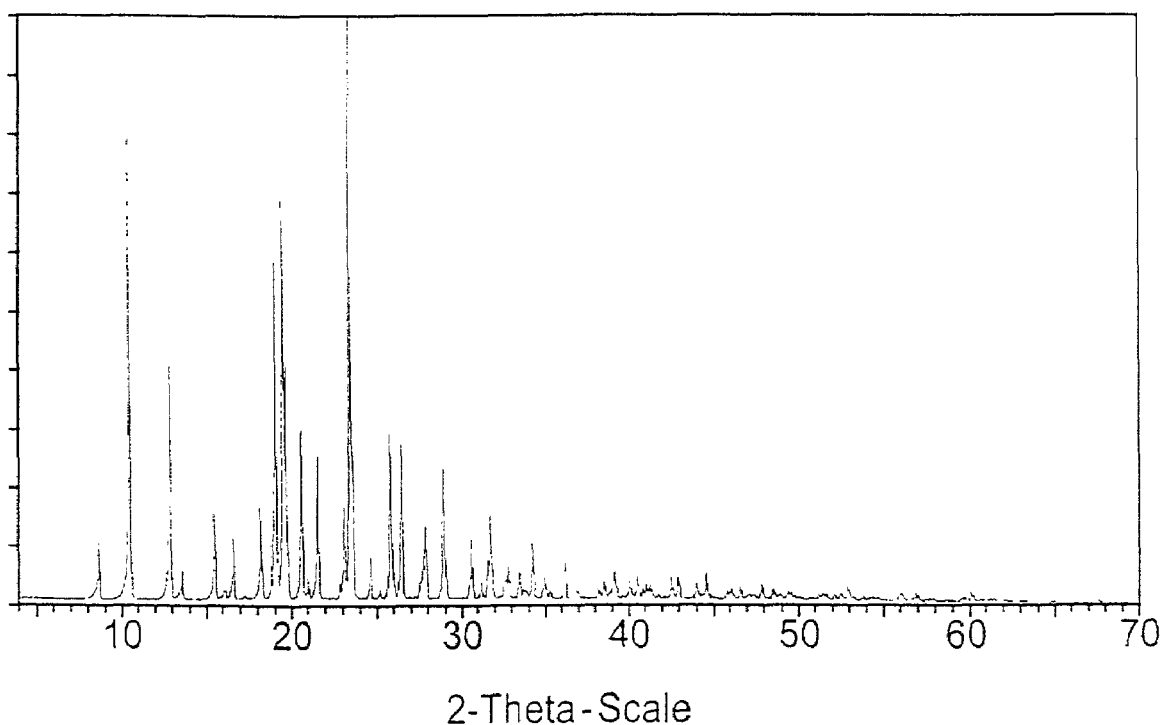

CRYSTALLINE CHOLINE ASCORBATE

The invention relates to crystalline choline ascorbate, in particular choline ascorbate in the form of crystals free from water of crystallization, processes for its preparation and its use.

Choline $\{[(H_3C)_3N^+\text{---}CH_2\text{---}CH_2\text{---}OH]OH^-\}$ is the basic constituent of phospholipids of the photoglyceride type and is widely distributed in the plant and animal kingdoms. Choline acts as an important factor in biochemical processes, for example in methylations. In animals, its deficiency leads to the formation of fatty liver.

Choline is principally used in the form of choline chloride or choline bitartrate in drug preparations for arterial calcification and liver parenchymal damage. In animal nutrition, choline chloride is an important feed additive.

Choline salts of organic acids, for example the abovementioned choline bitartrate, or choline salicylate, choline hydrogen citrate and choline ascorbate are described, inter alia, in EP-A-0 812 821.

The synthesis of choline ascorbate is subject-matter of U.S. Pat. No. 2,823,166 and CH 490322. However, the preparation processes described in these patent publications give a choline ascorbate which can only be isolated as a highly viscous oil, whose purity and stability is not always sufficient for use in the food and pharmaceutical sectors. In addition, the use of such an oil as animal feed or as an additive, for example in multivitamin tablets, frequently leads to application problems.

It is an object of the present invention, therefore, to provide a stable and high-purity form of choline ascorbate which does not have the abovementioned disadvantages of the prior art.

We have found that this object is achieved by providing crystalline choline ascorbate, preferably choline ascorbate in the form of crystals free from water of crystallization.

The inventive crystals were subjected to an X-ray diffraction analysis using Cu K-alpha-radiation.

The inventive crystals have, as most intense line in the 2 Θ X-ray powder diffractogram in the range between 3.40 and 4.70 Å a line at d=3.80 Å.

The inventive crystalline choline ascorbate in addition has an intensity ratio of the diffraction lines at d=3.80 Å and d=4.55 Å of at least 0.5, preferably at least 0.6, particularly preferably at least 0.7, and at d=3.80 Å and d=4.67 Å, at least 0.4, preferably at least 0.5, particularly preferably at least 0.6.

In addition to the diffraction lines at d=3.80 Å, 4.55 Å and 4.67 Å, the crystals exhibit other lines at d=3.46 Å, 3.78 Å, 6.91 Å, 8.49 Å and 10.29 Å.

The choline ascorbate crystals claimed in the context of the invention have a purity of >98%, preferably greater than >99%, particularly preferably >99.5%. In contrast to the choline ascorbate occurring as oil, the inventive crystals are only slightly hygroscopic.

Particle size measurements have shown that from 20 to 100% of the choline ascorbate crystals claimed in the invention have a particle size in the range from 10 to 2000 µm, preferably from 50 to 1000 µm, particularly preferably from 100 to 800 µm, very particularly preferably in the range from 100 to 600 µm.

For determining the size distribution of choline ascorbate crystals, both sieve analysis and laser diffraction spectrometry are suitable, the latter especially for measuring the fine-grained particles. The results of the particle size measurements obtained are volume distributions and thus mass distributions.

The crystalline salt is distinguished by combining two important active compounds for human and animal nutrition in one molecule in a stable high-purity and readily bioavailable form.

The invention also relates to a process for preparing crystalline choline ascorbate by reacting ascorbic acid with trimethylamine and ethylene oxide, which comprises carrying out the reaction in the temperature range from −20° C. to 80° C., preferably from −10° C. to 40° C., particularly preferably from 0° C. to 30° C.

The process further comprises carrying out the reaction in a water-miscible organic solvent or in a mixture of water and a water-miscible organic solvent. The proportion of water in the solvent can be from 0 to 50% by weight, preferably from 0 to 10% by weight.

Water-miscible solvents here are especially water-miscible, thermally stable, volatile solvents containing only carbon, hydrogen and oxygen, such as alcohols, ethers, esters, ketones and acetals. Preferably, solvents are used that are at least 10% water-miscible, have a boiling point below 200° C. and/or have less than 10 carbons. Particularly preferably, methanol, ethanol, n-propanol, isopropanol, 1-methoxy-2-butanol, 1-propoxy-2-propanol, tetrahydrofuran or acetone is used. Very particular preference is given to methanol and ethanol.

The molar ratio of the reaction partners trimethylamine: ascorbic acid:ethylene oxide is in the range 0.9 to 1.1:0.9 to 1.1:0.9 to 2.0, preferably in the range 1:1:1.5, particularly preferably in the range 1:1:1.2.

In a particular embodiment of the inventive process, choline ascorbate is crystallized in one of the abovementioned solvents used for the reaction.

It is also possible first to react trimethylamine and ethylene oxide in a water-miscible organic solvent, or in a mixture of water and a water-miscible organic solvent, at temperatures in the range from −20° C. to 80° C., preferably from −10° C. to 40° C., particularly preferably in a temperature range from 0° C. to 30° C., and then to convert this solution into choline ascorbate by adding a stoichiometric amount of ascorbic acid, and to crystallize this out.

As a further possible preparation variant, choline chloride may also be reacted with sodium ascorbate in a water-miscible organic solvent or in a mixture of water and a water-miscible organic solvent at temperatures in the range from −20° C. to 80° C., preferably from −10° C. to 40° C., particularly preferably in a temperature range from 0° C. to 30° C., to give the crystalline choline ascorbate. The sodium chloride formed in this process is filtered off before crystallizing out the product of value. In the presence of a basic chloride-selective ion exchanger, furthermore, the formation of the by product NaCl may be avoided.

The invention also relates to crystalline choline ascorbate obtainable by one of the abovementioned processes.

The invention also relates to the use of crystalline choline ascorbate for producing drugs, in particular preparations for combating liver cirrhosis or other liver disorders.

The invention also relates to the use of crystalline choline ascorbate as additive in foods, animal feeds or as a component in food supplements, for example in multivitamin preparations such as tablets or gelatin capsules.

The content of crystalline choline ascorbate both in the drugs and in the food supplements, for example in multivitamin tablets, can be in the range from 1 to 750 mg, preferably from 2 to 450 mg, particularly preferably from 5 to 225 mg, very particularly preferably in the range from 10 to 150 mg.

In tablets where only choline ascorbate is present, the choline ascorbate content can be in the range from 50 to 1500 mg.

The inventive crystalline choline ascorbate, its preparation process and its use will be described in more detail with reference to the examples below.

EXAMPLE 1

0.2 mol of ascorbic acid was added with cooling to 0° C. to 0.2 mol of trimethylamine in methanol (25% strength by weight). 0.2 mol of ethylene oxide gas was added to this mixture in such a manner that the reaction temperature did not exceed 0-5° C. After the reaction was completed, the reactor was flushed with nitrogen and further stirred at a temperature from 0 to 5° C. The choline ascorbate formed crystallized out of the reaction mixture, was filtered off, washed with methanol and, for further purification, recrystallized in methanol. Colorless crystals were obtained in a yield of 80%, having a melting point from 123.5° to 124.4° C. Using elemental analysis, $^{13}$C-NMR spectroscopy and single-crystal structure analysis, the crystals were characterized as choline ascorbate (anhydrous).

FIG. 1 shows an X-ray powder diffractogram of the crystalline choline ascorbate prepared in accordance with example 1 (measured using a Siemens diffractometer D5000, reflection measurement).

EXAMPLE 2

0.3 mol of ascorbic acid was added with cooling to 0° C. to 0.3 mol of trimethylamine in methanol (25% strength by weight). 0.45 mol of ethylene oxide gas was added to this mixture in such a manner that the reaction temperature did not exceed 0-5° C. After the reaction was completed the reactor was flushed with nitrogen and further stirred at a temperature from 0 to 5° C. The choline ascorbate formed crystallized out of the reaction mixture, was filtered off, washed with methanol and, for further purification, was recrystallized in methanol. Colorless crystals were obtained in a yield of 85%, having a melting point from 123.5° to 124.4° C.

EXAMPLE 3

0.2 mol of ascorbic acid and 6% by weight of water were added with cooling to 0° C. to 0.2 mol of triethylamine in methanol (25% strength by weight). 0.2 mol of ethylene oxide gas was added to this mixture in such a manner that the reaction temperature did not exceed 0-5° C. After the reaction was completed, the reactor was flushed with nitrogen and further stirred at a temperature from 0 to 5° C. The choline ascorbate formed crystallized out of the reaction mixture, was filtered off, washed with methanol and, for further purification, recrystallized in methanol. Colorless crystals having a melting point of 124° C. were obtained.

EXAMPLE 4

Multivitamin tablets of the following composition:

| | |
|---|---|
| β-Carotene | 5 mg |
| Vitamin E | 10 mg |
| Vitamin C | 60 mg |
| Vitamin D | 1.2 mcg |
| Thiamin | 1.4 mg |
| Riboflavin | 1.6 mg |
| Pyridoxine HCl | 2.2 mg |
| Vitamin B$_{12}$ | 1 mcg |
| Niacin | 18 mg |
| Pantothenic acid | 6 mg |
| Folic acid | 200 mcg |
| Biotin | 150 mcg |
| Choline ascorbate* | 1.2 mg |
| Magnesium | 100 mg |
| Zinc | 15 mg |
| Manganese | 2.5 mg |
| Selenium | 62 mcg |

*prepared in accordance with example 1

EXAMPLE 5

Multivitamin tablets of the following composition:

| | |
|---|---|
| β-Carotene | 5 mg |
| Vitamin E | 10 mg |
| Vitamin D | 1.2 mcg |
| Thiamin | 1.4 mg |
| Riboflavin | 1.6 mg |
| Pyridoxine HCl | 2.2 mg |
| Vitamin B$_{12}$ | 1 mcg |
| Niacin | 18 mg |
| Pantothenic acid | 6 mg |
| Folic acid | 200 mcg |
| Biotin | 150 mcg |
| Choline ascorbate* | 150 mg |
| Magnesium | 100 mg |
| Zinc | 15 mg |
| Manganese | 2.5 mg |
| Selenium | 62 mcg |

*prepared in accordance with example 1

EXAMPLE 6

Multivitamin tablets of the following composition:

| | |
|---|---|
| Vitamin C | 500 mg |
| Thiamin | 100 mg |
| Riboflavin | 100 mg |
| Niacin | 100 mg |
| Vitamin B$_6$ | 100 mg |
| Vitamin B$_{12}$ | 500 mcg |
| Pantothenic acid | 100 mg |
| Folic acid | 400 mcg |
| Biotin | 50 mcg |
| Choline ascorbate* | 500 mg |

*prepared in accordance with example 1

We claim:

1. A process for preparing choline ascorbate, wherein the choline ascorbate is obtained in form of anhydrous crystals having diffraction lines at d=3.80 Å and 4.55 Å, and having diffraction lines which are most intense in a range between 3.40 and 4.70 Å, in a 2 Θ X-ray powder diffractogram and having a melting point from 123.5 to 124.4° C. or in the range from 123.5 to 124.4° C., which process comprises a) providing a mixture of ascorbic acid, trimethylamine and a solvent, b) adding to the mixture gaseous ethylene oxide, and
c) crystallizing the choline ascorbate, wherein stages (a) and (b) are carried out at a temperature of from 0° C. to 5° C., and
the solvent is a water miscible organic solvent or is a mixture of said organic solvent and water.

2. The process of claim 1, wherein the solvent is a water miscible organic solvent.

3. The process of claim 1, wherein the choline ascorbate is crystallized from the solvent employed in stage (a).

* * * * *